US00PP36289P2

(12) United States Plant Patent
Mousa

(10) Patent No.: US PP36,289 P2
(45) Date of Patent: Dec. 3, 2024

(54) ***BEGONIA* PLANT NAMED 'Dobeciupblu'**

(50) Latin Name: ***Begonia boliviensis* X *Begonia tuberhybrida***
Varietal Denomination: Dobeciupblu

(71) Applicant: DUMMEN GROUP B.V., De Lier (NL)

(72) Inventor: Rami Mousa, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/444,723

(22) Filed: Feb. 18, 2024

(51) Int. Cl.
*A01H 5/02* (2018.01)
*A01H 6/18* (2018.01)

(52) U.S. Cl.
USPC ..... Plt./344

(58) Field of Classification Search
USPC ..... Plt./343, 344
See application file for complete search history.

*Primary Examiner* — Susan McCormick Ewoldt
(74) *Attorney, Agent, or Firm* — C. Anne Whealy

(57) ABSTRACT

A new and distinct cultivar of *Begonia* plant named 'Dobeciupblu', characterized by its relatively compact, semi-upright and mounded plant habit; moderately vigorous growth habit and moderate growth rate; strong branching habit; dark brownish green-colored leaves; freely and continuously flowering habit; and medium-sized double-type flowers with petals that are pale yellow in color with dark pink-colored edges and petaloids that are light yellowish pink in color.

1 Drawing Sheet

Botanical designation: *Begonia boliviensis* X *Begonia tuberhybrida.*

Cultivar denomination: 'DOBECIUPBLU'.

STATEMENT REGARDING PRIOR DISCLOSURES BY INVENTOR and APPLICANT/ASSIGNEE

An European Community Plant Breeder's Rights application for the instant plant was filed by the Applicant/Assignee, Dümmen Group B.V. of De Lier, The Netherlands on Oct. 26, 2023, application number 2023/2271. Foreign priority is claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Begonia* plant, botanically known as *Begonia boliviensis* X *Begonia tuberhybrida*, commercially referred to as a Hybrid *Begonia* and hereinafter referred to by the name 'Dobeciupblu'.

The new *Begonia* plant is a product of a planned breeding program conducted by the Inventor in De Lier, The Netherlands. The objective of the breeding program was to develop new freely flowering *Begonia* plants with strong branches and attractive flowers.

The new *Begonia* plant originated from a cross-pollination made by the Inventor during the autumn of 2018 of a proprietary selection of *Begonia* x *boliviensis* X *Begonia tuberhybrida* identified as code number BG16-000027-001, not patented, as the female, or seed, parent with a proprietary selection of *Begonia* x *boliviensis* X *Begonia tuberhybrida* identified as code number BG16-000035-001, not patented, as the male or pollen, parent. The new *Begonia* plant was discovered and selected by the Inventor as a single flowering plant from within the progeny of the stated cross-pollination in a controlled greenhouse environment in De Lier, The Netherlands during the spring of 2019.

Asexual reproduction of the new *Begonia* plant by vegetative tip cuttings in a controlled greenhouse environment in De Lier, The Netherlands since the autumn of 2019 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobeciupblu'. These characteristics in combination distinguish 'Dobeciupblu' as a new and distinct *Begonia* plant:

1. Relatively compact, semi-upright and mounded plant habit.
2. Moderately vigorous growth habit and moderate growth rate.
3. Strong branching habit.
4. Dark greenish brown-colored leaves.
5. Freely and continuously flowering habit.

6. Medium-sized double-type flowers with petals that are pale yellow in color with dark pink-colored edges and petaloids that are light yellowish pink in color.

Plants of the new *Begonia* can be compared to plants of the female parent selection. In side-by-side comparisons, plants of the new *Begonia* differ primarily from plants of the female parent selection in the following characteristics:

1. Plants of the new *Begonia* are more freely branching than plants of the female parent selection.
2. Flowers of plants of the new *Begonia* have pale yellow-colored petals with dark pink-colored edges and yellowish pink-colored petaloids whereas flowers of plants of the female parent selection are orange in color.
3. Plants of the new *Begonia* have shorter flower pedicels than plants of the female parent selection.

Plants of the new *Begonia* can be compared to plants of the male parent selection. In side-by-side comparisons, plants of the new *Begonia* differ primarily from plants of the male parent selection in flower color as plants of the new *Begonia* have flower petals that are pale yellow in color with dark pink-colored edges and petaloids that are light yellowish pink in color whereas flowers of plants of the male parent selection are orangish pink in color.

Plants of the new *Begonia* can be compared to plants of *Begonia boliviensis* X *Begonia tuberhybrida* 'I'CONIA Bacio Peach', not patented. In side-by-side comparisons, plants of the new *Begonia* differ primarily from plants of 'I'CONIA Bacio Peach' in the following characteristics:

1. Plants of the new *Begonia* are more freely branching than plants of 'I'CONIA Bacio Peach'.
2. Plants of the new *Begonia* have larger leaves than plants of 'I'CONIA Bacio Peach'.
3. Plants of the new *Begonia* are more freely flowering than plants of 'I'CONIA Bacio Peach'.
4. Flowers of plants of the new *Begonia* have more petaloids than flowers of plants of 'I'CONIA Bacio Peach'.
5. Flowers of plants of the new *Begonia* have pale yellow-colored petals with dark pink-colored edges and yellowish pink-colored petaloids whereas flowers of plants of 'I'CONIA Bacio Peach' are soft yellow to peach in color.
6. Plants of the new *Begonia* have shorter flower pedicels than plants of 'I'CONIA Bacio Peach'.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant. The photograph is a side perspective view of a typical flowering plant of 'Dobeciupblu' grown in a container.

DETAILED BOTANICAL DESCRIPTION

Plants used for the aforementioned photograph and following observations and measurements were grown in 12-cm containers during the summer in a glass-covered greenhouse in De Lier, The Netherlands. During the production of the plants, day temperatures ranged from 20° C. to 35° C., night temperatures ranged from 17° C. to 25° C. and minium light levels were 135 watt/m$^2$. Plants were twelve weeks old when the photograph and the description were taken. In the following description, color references are made to The Royal Horticultural Society Colour Chart, Fifth Edition, except where general terms of ordinary dictionary significance are used.

Botanical classification: *Begonia boliviensis* X *Begonia tuberhybrida* 'Dobeciupblu'.

Parentage:

*Female, or seed, parent*.—Proprietary selection of *Begonia boliviensis* X *Begonia tuberhybrida* identified as code number BG16-000027-001, not patented.

*Male, or pollen, parent*.—Proprietary selection of *Begonia boliviensis* X *Begonia tuberhybrida* identified as code number BG16-000035-001, not patented.

Propagation:

*Type*.—By vegetative tip cuttings.

*Time to initiate roots, summer*.—About 18 days at temperatures about 22° C. to 30° C.

*Time to initiate roots, winter*.—About 21 days at temperatures about 20° C. to 22° C.

*Time to produce a rooted young plant, summer*.—About 22 to 25 days at temperatures about 22° C. to 30° C.

*Time to produce a rooted young plant, winter*.—About 25 to 28 days at temperatures about 20° C. to 22° C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Relatively compact, semi-upright to mounded plant habit; freely basal branching with about three primary lateral branches each with about four secondary lateral branches; moderately vigorous growth habit and moderate growth rate.

*Plant height, soil level to top of foliar plane*.—About 20 cm.

*Plant height, soil level to top of floral plane*.—About 23 cm.

*Plant width*.—About 28 cm.

*Lateral branch description*.—Length: About 13 cm. Diameter: About 1.1 cm. Internode length: About 1 cm to 2 cm. Texture and luster: Pubescent; semi-glossy. Aspect: Mostly upright. Strength: Moderately strong, flexible. Color, developing: Close to 146C. Color, developed: Close to 146A.

*Leaf description*.—Arrangement: Alternate, simple. Length: About 14 cm. Width: About 6 cm. Shape: Lanceolate. Apex: Narrowly acute. Base: Oblique. Margin: Serrate; sinuses medium in depth and divergent. Texture and luster, upper and lower surfaces: Pubescent; semi-glossy. Venation pattern: Palmate; reticulate. Color: Developing and fully expanded leaves, upper surface: Close to 139A variably tinged with close to 200A; venation, close to 141B. Developing and fully expanded leaves, lower surface: Close to 185B; venation, close to 141C. Petioles: Length: About 6 cm. Diameter: About 5 mm. Texture and luster, upper and lower surfaces: Smooth, glabrous; semi-glossy. Strength: Moderately strong; flexible. Color, upper surface: Close to 152B. Color, lower surface: Close to 152C.

Flower description:

*Flowering habit*.—Double-type flowers arranged in axillary cymes; freely flowering habit with typically about three flowers per inflorescence and about 58 open flowers and flower buds per plant at one time; flowers face mostly upright to outwardly.

*Fragrance*.—None detected.

*Natural flowering season*.—Plants begin flowering about eight weeks after planting; long flowering period, in the garden plants flower freely and continuously from the late spring throughout the summer in Northern Europe and can be flowered year-round in greenhouses under short nyctoperiods.

*Flower longevity*.—Depending on temperature, individual flowers last about four to five weeks on the plant; flowers persistent.

*Inflorescence height*.—About 7.5 cm.

*Inflorescence diameter*.—About 10 cm.

*Flower buds*.—Length: About 2.5 cm to 3 cm. Diameter: About 2 cm. Shape: Ovoid. Texture and luster: Smooth, glabrous; semi-glossy. Color: Close to 145C.

*Flower size*.—Diameter: About 7.8 cm. Depth (height): About 2.5 cm.

*Petals*.—Quantity per flower and arrangement: Typically four to five per flower arranged in a single whorl. Length: About 4.2 cm. Width: About 4 cm. Shape: Obovate. Apex: Rounded and emarginate. Base: Cuneate and truncate. Margin: Entire; not undulate. Texture and luster, upper surface: Smooth, glabrous; matte. Texture and luster, lower surface: Smooth, glabrous; semi-glossy. Color: When opening, upper and lower surfaces: Close to 8C; petal edges, close to 53D; venation, close to 10D; color does not change with subsequent development. Fully opened, upper and lower surfaces: Close to 8D; petal edges, close to 50B; venation, close to 10D; color does not change with subsequent development.

*Petaloids*.—Quantity per flower and arrangement: Typically 15 per flower arranged in about three or four whorls. Length: About 2 cm. Width: About 1 cm. Shape: Obovate. Apex: Rounded, obtuse. Base: Cuneate. Margin: Entire; slightly undulate. Texture and luster, upper and lower surfaces: Smooth, glabrous; semi-glossy. Color: When opening, upper and lower surfaces: Close to 9A becoming closer to 29B with development. Fully opened, upper surface: Close to 29C; venation, close to 23A; color becoming closer to 29B with subsequent development. Fully opened, lower surface: Close to 29C to 29D; venation, close to 23B; color becoming closer to 29C with subsequent development.

*Sepals*.—Quantity per flower and arrangement: Typically two per flower arranged in a single whorl. Length: About 1.5 cm. Width: About 2 cm. Shape: Obovate. Apex: Rounded and emarginate. Base: Cuneate and truncate. Margin: Entire. Texture and luster, upper and lower surfaces: Smooth, glabrous; semi-glossy. Color: When opening, upper and lower surfaces: Close to 141D. Fully opened, upper and lower surfaces: Close to 141D.

*Peduncles*.—Length: About 8.5 cm. Diameter: About 5 mm. Aspect: Semi-upright. Strength: Moderately strong; flexible. Texture and luster: Smooth, glabrous; glossy. Color: Close to 144D.

*Pedicels*.—Length: About 1 cm to 2.5 cm. Diameter: About 2 mm. Aspect: Upright to outwardly. Strength: Moderately strong; flexible. Texture and luster: Smooth, glabrous; glossy. Color: Close to 145B.

*Reproductive organs*.—Stamens: Quantity per flower: About 15. Filament length: About 8 mm. Filament color: Close to 13A. Anther length: About 2 mm. Anther shape: Oval. Anther color: Close to 15A. Pollen amount: None observed. Pistils: Quantity per flower: About three. Pistil length: About 7 mm. Stigma diameter: About 5 mm. Stigma shape: Bilobed, curled. Stigma color: Close to 17C. Style length: About 4.5 mm. Style color: Close to 14B. Ovary color: Close to 145A. Seeds: Plants of the new *Begonia* have been observed to produce seeds, however, seeds are "dust-like" and too minute to quantify and describe.

Pathogen & pest resistance: To date, resistance to pathogens and pests common to *Begonia* plants has not been observed on plants of the new *Begonia*.

Temperature tolerance: Plants of the new *Begonia* have been observed to tolerate temperatures ranging from about 10° C. to about 35° C.

It is claimed:

1. A new and distinct *Begonia* plant named 'Dobeciupblu' as illustrated and described.

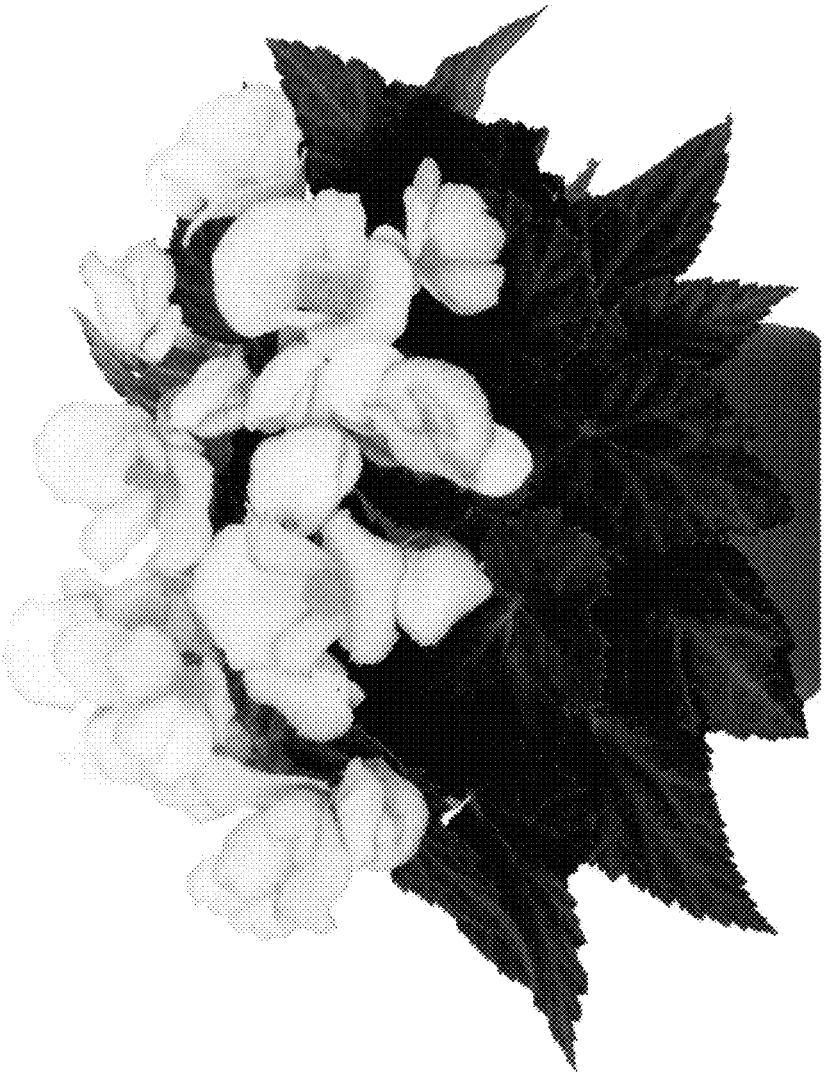

* * * * *